(12) United States Patent
Hefetz

(10) Patent No.: US 7,408,163 B2
(45) Date of Patent: Aug. 5, 2008

(54) METHODS AND SYSTEMS FOR MEDICAL IMAGING

(75) Inventor: Yaron Hefetz, Herzeliya (IL)

(73) Assignee: General Electric Company, Schenectady, NY (US)

( * ) Notice: Subject to any disclaimer, the term of this patent is extended or adjusted under 35 U.S.C. 154(b) by 223 days.

(21) Appl. No.: 11/358,580

(22) Filed: Feb. 21, 2006

(65) Prior Publication Data

US 2007/0194240 A1 Aug. 23, 2007

(51) Int. Cl.
G01T 1/166 (2006.01)
G01T 1/20 (2006.01)
H01L 27/146 (2006.01)

(52) U.S. Cl. ............ 250/363.04; 250/363.01; 250/370.08

(58) Field of Classification Search ............ 250/363.04, 250/363.01, 370.08
See application file for complete search history.

(56) References Cited

U.S. PATENT DOCUMENTS

| 5,444,252 A | 8/1995 | Hug et al. |
| 5,486,760 A | 1/1996 | Selleri et al. |
| 5,777,332 A | 7/1998 | Lonn et al. |
| 6,194,725 B1 | 2/2001 | Colsher et al. |
| 6,577,890 B1 * | 6/2003 | Hayes et al. ............... 600/436 |

* cited by examiner

Primary Examiner—David P. Porta
Assistant Examiner—Mindy Vu
(74) Attorney, Agent, or Firm—Dean D. Small; The Small Patent Law Group

(57) ABSTRACT

Methods and systems for imaging a patient using an imaging system is provided. The method includes rotating a detector assembly about an examination axis of the imaging system, maintaining a first detector of the detector assembly at a first distance from the patient while receiving imaging data from the patient, and maintaining a second detector of the detector assembly at a second distance from the patient while receiving imaging data from the patient wherein the second distance is greater than the first distance and wherein the resolution of the imaging data from the first detector is smaller than the resolution of the imaging data from the second detector due to the difference between the first distance and the second distance.

20 Claims, 2 Drawing Sheets

METHODS AND SYSTEMS FOR MEDICAL IMAGING

BACKGROUND OF THE INVENTION

This invention relates generally to imaging systems, and more particularly to methods and apparatus for medical imaging with improved resolution.

Diagnostic nuclear imaging is used to study radionuclide distribution in a subject, such as a patient. Typically, one or more radiopharmaceuticals or radioisotopes are injected into the subject. Gamma camera detector heads, typically including a collimator, are placed adjacent to a surface of the subject to monitor and record emitted radiation. At least some known gamma camera detector heads are rotated around the subject to monitor the emitted radiation from a plurality of directions. The monitored radiation data from the plurality of directions is reconstructed into a three dimensional image representation of the radiopharmaceutical distribution within the subject.

Generally, the resolution of a gamma camera degrades with increasing distance between the imaged organ and the detector. Therefore, it is desirable to place the gamma camera as close as possible to the patient to facilitate minimizing the loss of resolution. At least some known imaging systems use non-circular orbits, such as oval or elliptical orbits to facilitate maintaining the detectors positioned close to the patient during a scan. When the imaging system is configured for example, with a pair of gamma cameras in an "L" mode as is done when imaging the heart, and other organs, the gamma cameras are configured so they essentially touch one another along adjacent edges. Typical gamma cameras comprise a large scintillation crystal of NaI optically coupled to an array of Photo-Multiplying Tube (PMT). Signals from the array of PMTs are processed to yield the location of the scintillation event on the crystal in what is known as "Anger" camera, for example as disclosed in U.S. Pat. No. 3,011,057. Because of this construction, the gamma camera is less responsive near an outer periphery of the detector. The gamma camera detector is sized larger than the viewing area, and a volume of missing data is created proximate a surface of each detector where the volume is "seen" from only one of the detectors. Generally, the body of the patient is maintained spaced away from the surface of the detectors to avoid "missing data" that causes artifacts in the reconstructed image.

BRIEF DESCRIPTION OF THE INVENTION

In one embodiment, a method for imaging a patient using an imaging system includes rotating a detector assembly about an examination axis of the imaging system, maintaining a first detector of the detector assembly at a first distance from the patient while receiving imaging data from the patient, and maintaining a second detector of the detector assembly at a second distance from the patient while receiving imaging data from the patient wherein the second distance is greater than the first distance and wherein the resolution of the imaging data from the first detector is smaller than the resolution of the imaging data from the second detector due to the difference between the first distance and the second distance.

In another embodiment, an imaging system detector assembly includes a first detector including a radially inwardly facing surface, a radially outwardly facing surface, and a sidewall extending therebetween. The detector further includes a central detector area surrounded by a region of variable response that forms the sidewall and a portion of the surfaces adjacent the sidewall. The detector assembly further includes a second detector including a radially inwardly facing surface, a radially outwardly facing surface, and a sidewall extending therebetween. The second detector further includes a central detector area surrounded by a region of variable response that forms the sidewall and a portion of the surfaces adjacent the sidewall wherein the first and second detectors coupled in an orientation substantially orthogonal with respect to each other such that the sidewall of the first detector is positioned adjacent to the region of variable response that forms the portion of the surface adjacent the sidewall of the second detector.

In yet another embodiment, an imaging system includes a gantry with a patient bore therethrough, a rotor rotatably coupled to the gantry wherein the rotor is configured to rotate about a longitudinal axis of the bore, the rotor includes a first detector including a radially inwardly facing surface, a radially outwardly facing surface, and a sidewall extending therebetween, the first detector further includes a central detector area surrounded by a region of variable response that forms the sidewall and a portion of the surfaces adjacent the sidewall. A second detector includes a radially inwardly facing surface, a radially outwardly facing surface, and a sidewall extending therebetween, the second detector further includes a central detector area surrounded by a region of variable response that forms the sidewall and a portion of the surfaces adjacent the sidewall wherein the first and second detectors are coupled in an orientation substantially orthogonal with respect to each other such that the sidewall of the first detector is positioned adjacent to the region of variable response that forms the portion of the surface adjacent the sidewall of the second detector.

DETAILED DESCRIPTION OF THE INVENTION

Figure 1:
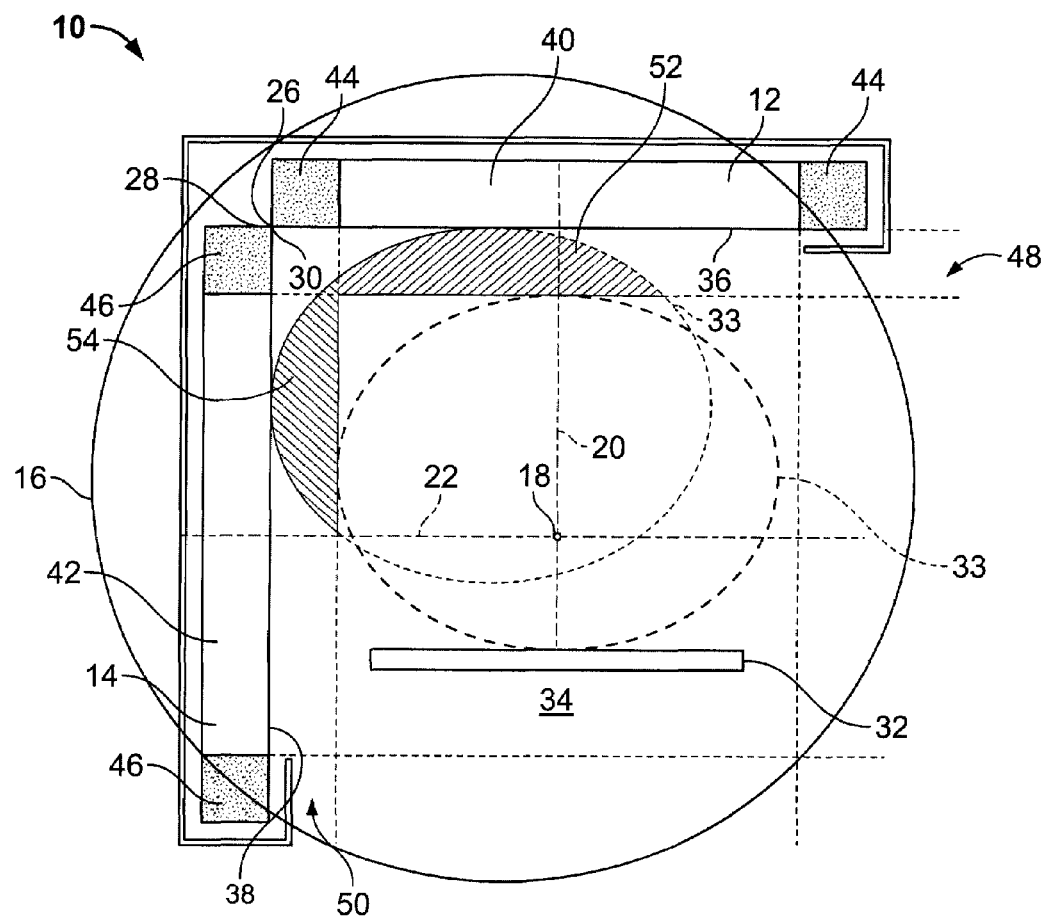
FIG. 1 is a front elevation view of a nuclear medicine imaging system 10.

FIG. 1 is a front elevation view of a nuclear medicine imaging system 10. System 10 includes first and second gamma cameras 12 and 14 mounted on a gantry 16 for rotation about an axis 18. Camera 12 is centered on a camera axis 20 while camera 14 is centered on a camera axis 22, axes 20 and 22 intersecting at rotation axis 18. Adjacent corners 26 and 28 of cameras 12 and 14, respectively, contact at a point 30 when cameras 12 and 14 are configured in an L mode. A support table 32, for a patient 33 is positioned within an imaging area 34 which is in the field of view of each of cameras 12 and 14.

Gamma cameras 12 and 14 each include a central detector area 40 and 42, respectively, surrounded by a relatively narrow detector region of variable response 44 and 46, respectively, around the camera perimeter that is responsive to radiation in a relativity unpredictable degree. Gamma cameras 12 and 14 also include a collimator 36 and 38, respectively, closely coupled to central detector areas 40 and 42 and detector regions of variable response 44 and 46. Regions of variable response 44 and 46 prevent data collection in a missing data area 48 and 50, respectively, of imaging area 34. Missing data areas 48 and 50 extend orthogonally from a face of detector regions of variable response 44 and 46, respectively.

In the exemplary embodiment, gamma cameras 12 and 14 are fabricated to a larger area than patient 33 to avoid "missing data."

A resolution of gamma cameras 12 and 14 is determined by adding in quadrateure an intrinsic resolution of the detector (3-4 mm) and the collimator resolution. Collimator resolution degrades linearly with distance from the collimator and is given by the distance multiplied by the angular acceptance of the collimator holes.

$$\text{Resolution} \approx \sqrt{\begin{array}{l}(\text{distance} * \text{collimator\_acceptance\_angle})^2 + \\ (\text{detector\_intrinsic\_resolution})^2 + \\ \text{collimator\_hole\_size}^2\end{array}}$$

Accordingly, it is important to keep the inspected body as close as possible to the face of the collimator. However, with gamma cameras 12 and 14 joined at adjacent corners 26 and 28, a portion of imaging area 34, proximate one of the gamma cameras surface is not "covered" by the other gamma camera. For example, a portion 52 is not covered by gamma camera 14 and a portion 54 is not covered by gamma camera 12.

In practice, patient 33 is maintained a distance away from the surface of gamma cameras 12 and 14 to avoid "missing data" that causes artifacts in the reconstructed image.

Figure 2:
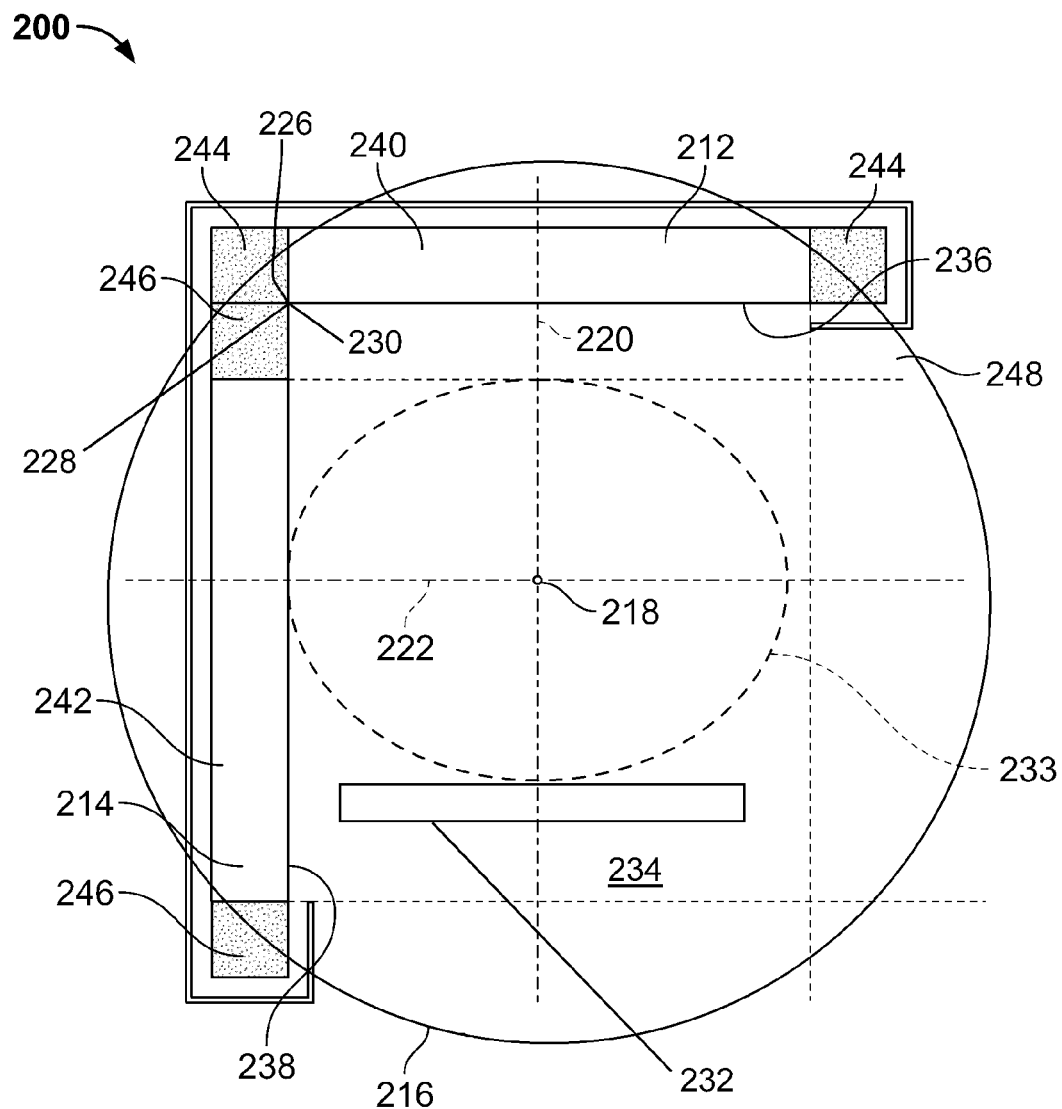
FIG. 2 is a front elevation view of a nuclear medicine imaging system 200 in accordance with an exemplary embodiment of the present invention.

FIG. 2 is a front elevation view of a nuclear medicine imaging system 200 in accordance with an exemplary embodiment of the present invention. System 200 includes first and second gamma cameras 212 and 214 mounted on a gantry 216 for rotation about an axis 218. Camera 212 is centered on a camera axis 220 while camera 214 is centered on a camera axis 222, axes 220 and 222 intersecting at rotation axis 218. Adjacent corners 226 and 228 of cameras 212 and 214, respectively, contact at a point 230 when cameras 212 and 214 are configured in an L mode. A support table 232, for a patient 233 is positioned within an imaging area 234 which is in the field of view of each of cameras 212 and 214.

Gamma cameras 212 and 214 each include a central detector area 240 and 242, respectively, surrounded by a relatively narrow detector region of variable response 244 and 246, respectively, around the camera perimeter that is responsive to radiation in a relativity unpredictable degree. Gamma cameras 212 and 214 also include a collimator 236 and 238, respectively, closely coupled to central detector areas 240 and 242 and detector regions of variable response 244 and 246. In the exemplary embodiment, gamma cameras 212 and 214 are oriented in a staggered configuration with respect to their respective detector regions of variable response 244 and 246 such that a missing data area 248 is formed orthogonally extending from only one of gamma cameras 212 and 214. The staggered configuration permits positioning a patient 233 closer to gamma camera 214 than in the orientation described with respect to the configuration of FIG. 1.

Regions of variable response 244 and 246 prevent data collection in a missing data area 248 and 50 (shown in FIG. 1), respectively, of imaging area 234 and 34 (shown in FIG. 1), respectively. Missing data areas extend orthogonally from a face of detector regions of variable response 244 and 246, or 44 and 46 (shown in FIG. 1). In the exemplary embodiment, gamma cameras 212 and 214 are fabricated to a larger area than patient 233 to avoid "missing data."Moreover, each of the gamma cameras 212 and 214 may include a radially inwardly facing surface and a radially outwardly facing surface, as well as a sidewall extending therebetween. In at least one embodiment, a radiation shield may at least partially cover the radially outwardly facing surfaces, the sidewalls of each of gamma cameras 212 and 214 that is not adjacent the other, and portions of the region of variable response 244 and 246, respectively, of the radially inner surface adjacent the sidewalls. The radiation shield may be formed of different matierals, for example, lead.

The staggered configuration permits the resolution of the reconstructed image to be facilitated being improved because half of the data was acquired with better resolution due to the patient being positioned closer to gamma camera 214. A resolution recovery method may be implemented during for example, an iterative reconstruction algorithm to account the resolution difference between the two data sets acquired by gamma cameras 212 and 214.

It is contemplated that the benefits of the various embodiments of the present invention accrue to all imaging systems, such as, for example, but not limited to, nuclear medicine imaging systems, PET, SPECT and dual-modality imaging systems.

The above-described embodiments of imaging a patient using an imaging system provide a cost-effective and reliable means for examining a patient. More specifically, the imaging system includes a plurality of gamma cameras in a staggered orientation with respect to each other such that a region of missing data is substantially eliminated. As a result, an imaging system is provided that facilitates improving the resolution of the gamma cameras.

Exemplary embodiments of imaging systems are described above in detail. The imaging system components illustrated are not limited to the specific embodiments described herein, but rather, components of each imaging system may be utilized independently and separately from other components described herein. For example, the imaging system components described above may also be used in combination with other imaging systems.

While the invention has been described in terms of various specific embodiments, those skilled in the art will recognize that the invention can be practiced with modification within the spirit and scope of the claims.

What is claimed is:

1. A method of imaging a patient using an imaging system, said method comprising:

rotating a detector assembly about an examination axis of the imaging system wherein the detector assembly includes a first detector and a second detector, each detector having a radially inward facing surface and sidewalls extending radially outwardly from the surface, the radially inward facing surfaces oriented in a fixed substantially orthogonal orientation with respect to each other during an entire imaging scan and wherein at least a portion of the sidewall of the first detector covers at least a portion of the inward facing surface of the second detector;

maintaining a first detector of the detector assembly at a first distance from the patient while receiving imaging data from the patient; and maintaining a second detector of the detector assembly at a second distance from the patient while receiving imaging data from the patient wherein the second distance is greater than the first distance.

2. A method in accordance with claim 1 wherein a region of variable response comprises a width from a detector sidewall to a central detector area, said method comprising maintaining a gap between said second detector and a patient substantially equal to the distance from said detector sidewall to said central detector area of said first detector.

3. A method in accordance with claim 1 wherein a region of variable response comprises a width from a detector sidewall to a central detector area, said method comprising maintaining said first detector a predetermined distance from a patient that is less than the distance from said sidewall to said central detector area of said second detector.

4. A method in accordance with claim 1 further comprising at least partially covering radially outwardly facing surfaces of said detectors, said sidewalls of each detector not adjacent the other detector, and portions of a region of variable response of the radially inner surface adjacent said sidewalls with a radiation shield.

5. A method in accordance with claim 1 further comprising at least partially covering radially outwardly facing surfaces of said detectors, said sidewalls of each detector not adjacent the other detector, and portions of a region of variable response of the radially inner surface adjacent said sidewalls with a radiation shield comprising lead.

6. A method in accordance with claim 1 wherein the resolution of the first detector is greater than the resolution of the second detector.

7. An imaging system detector assembly comprising:
a first detector comprising a radially inwardly facing surface, a radially outwardly facing surface, and a sidewall extending therebetween, said detector further comprising a central detector area surrounded by a region of variable response that forms the sidewall and a portion of the surface adjacent said sidewall; and
a second detector comprising a radially inwardly facing surface, a radially outwardly facing surface, and a sidewall extending therebetween, said detector further comprising a central detector area surrounded by a region of variable response that forms the sidewall and a portion of the surface adjacent said sidewall;
said first and second detectors fixedly coupled in an orientation substantially orthogonal with respect to each other during an entire imagine scan such that the sidewall of the first detector is positioned adjacent to the region of variable response that forms the portion of the surface adjacent the sidewall of the second detector.

8. An assembly in accordance with claim 7 wherein said region of variable response comprises a distance from said sidewall to said central detector area and wherein said assembly is configured to maintain a spacing between said second detector and a patient substantially equal to the distance from said sidewall to said central detector area of said first detector.

9. An assembly in accordance with claim 7 wherein said region of variable response comprises a distance from said sidewall to said central detector area and wherein said assembly is configured to maintain said first detector a predetermined distance from a patient that is less than the distance from said sidewall to said central detector area of said second detector.

10. An assembly in accordance with claim 7 further comprising a radiation shield at least partially covering said radially outwardly facing surfaces, said sidewalls of each detector not adjacent the other detector, and said portions of the region of variable response of the radially inner surface adjacent said sidewalls.

11. An assembly in accordance with claim 10 wherein said shield comprises lead.

12. An assembly in accordance with claim 7 wherein the resolution of the first detector and the resolution of the second detector are not equal.

13. An assembly in accordance with claim 7 wherein the resolution of the first detector is greater than the resolution of the second detector.

14. An imaging system comprising:
a gantry with a patient bore therethrough;
a rotor rotatably coupled to said gantry, said rotor configured to rotate about a longitudinal axis of said bore, said rotor comprising:
a first detector comprising a radially inwardly facing surface, a radially outwardly facing surface, and a sidewall extending therebetween, said detector further comprising a central detector area surrounded by a region of variable response that forms the sidewall and a portion of the surface adjacent said sidewall; and
a second detector comprising a radially inwardly facing surface, a radially outwardly facing surface, and a sidewall extending therebetween, said detector further comprising a central detector area surrounded by a region of variable response that forms the sidewall and a portion of the surface adjacent said sidewall;
said first and second detectors fixedly coupled in an orientation substantially orthogonal with respect to each other during an entire imaging scan such that the sidewall of the first detector is positioned adjacent to the region of variable response that forms the portion of the surface adjacent the sidewall of the second detector.

15. A system in accordance with claim 14 wherein said region of variable response comprises a distance from said sidewall to said central detector area and wherein said assembly is configured to maintain a spacing between said second detector and a patient substantially equal to the distance from said sidewall to said central detector area of said first detector.

16. A system in accordance with claim 14 wherein said region of variable response comprises a distance from said sidewall to said central detector area and wherein said assembly is configured to maintain said first detector a predetermined distance from a patient that is less than the distance from said sidewall to said central detector area of said second detector.

17. A system in accordance with claim 14 further comprising a radiation shield at least partially covering said radially outwardly facing surfaces, said sidewalls of each detector not adjacent the other detector, and said portions of the region of variable response of the radially inner surface adjacent said sidewalls.

18. A system in accordance with claim 17 wherein said shield comprises lead.

19. A system in accordance with claim 14 wherein the resolution of the first detector and the resolution of the second detector are not equal.

20. A system in accordance with claim 14 wherein the resolution of the first detector is greater than the resolution of the second detector.

* * * * *

UNITED STATES PATENT AND TRADEMARK OFFICE
CERTIFICATE OF CORRECTION

| | | |
|---|---|---|
| PATENT NO. | : 7,408,163 B2 | Page 1 of 1 |
| APPLICATION NO. | : 11/358580 | |
| DATED | : August 5, 2008 | |
| INVENTOR(S) | : Yaron Hefetz | |

It is certified that error appears in the above-identified patent and that said Letters Patent is hereby corrected as shown below:

Column 5, line 37, claim 7:

Please delete "during an entire imagine scan such that the sidewall of". Insert correction --during an entire imaging scan such that the sidewall of--

Signed and Sealed this

Twenty-first Day of October, 2008

JON W. DUDAS
*Director of the United States Patent and Trademark Office*